(12) United States Patent
Werner et al.

(10) Patent No.: US 6,455,553 B1
(45) Date of Patent: Sep. 24, 2002

(54) METHOD FOR TREATING A DEMYELINATING CONDITION

(75) Inventors: Peter Werner, New York; David Pitt, Bronx, both of NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/678,686

(22) Filed: Oct. 3, 2000

(51) Int. Cl.$^7$ ................................................ A61K 31/44
(52) U.S. Cl. ...................................... 514/356; 514/903
(58) Field of Search ........................... 514/356, 211.07, 514/255.04, 340, 400, 520

(56) References Cited

FOREIGN PATENT DOCUMENTS

WO          92/07564     *   5/1992

OTHER PUBLICATIONS

CA118:167285, Rayner et al, Immunology, 1993, 78(2), 273–8, abstract.*
CA117:124494, Barry et al, WO 9207564 A2, May. 14, 1992, abstract.*
CA132:88184, Turski et al, WO 2000001376 A2, Jan. 13, 2000, abstract.*
WPIDS AN 1998–053370, Behl et al, DE19624808 A1, Jan. 2, 1998, abstract.*
Akassoglou et al., Oligodendrocyte apoptosis and primary demyelination induced by local TNF/p55TNF receptor signaling in the central nervous system of transgenic mice. American Journal of Pathology, 153(3):801–13, Sep. 1998.
Cannella et al., The neuregulin, glial growth factor 2, diminishes autoimmune demyelination and enhances remyelination in a chronic relapsing model for multiple sclerosis. Proc. Natl. Acad. USA. 95:10100–105, Aug. 1998.
Pitt et al., Glutamate excitotoxicity in a model of multiple sclerosis. Nat. Med., 6(1):67–70, Jan. 2000, Abstract.
Werner et al., Glutamate excitotoxicity—a mechanism for axonal damage and oligodendrocyte death in multiple sclerosis? J. Neural Transm. Suppl., 60:375–85, 2000, Abstract.

* cited by examiner

*Primary Examiner*—Rebecca Cook
(74) *Attorney, Agent, or Firm*—Amster, Rothstein & Ebenstein

(57) ABSTRACT

The present invention provides a method for treating a demyelinating condition in a subject in need of treatment, by administering to the subject an amount of a $Ca^{2+}$-channel blocker effective to treat the demyelinating condition. The present invention is also directed to a method for treating a demyelinating condition in a subject in need of treatment, by administering to the subject a $Ca^{2+}$-channel blocker in combination with a glutamate inhibitor, in amounts effective to treat the demyelinating condition. Also disclosed is a pharmaceutical composition comprising a $Ca^{2+}$-channel blocker, a glutamate inhibitor, and a pharmaceutically-acceptable carrier. Additionally, the present invention provides a method for treating a demyelinating condition in a subject in need of treatment, by administering to the subject a $Ca^{2+}$-channel blocker in combination with a hypertensive agent, in amounts effective to treat the demyelinating condition. Finally, the present invention discloses a pharmaceutical composition comprising a $Ca^{2+}$-channel blocker, a hypertensive agent, and a pharmaceutically-acceptable carrier.

6 Claims, 1 Drawing Sheet

METHOD FOR TREATING A DEMYELINATING CONDITION

BACKGROUND OF THE INVENTION

Demyelination is a feature of many neurologic disorders. Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections [1, 23].

Central demyelination (demyelination of the CNS) occurs in several conditions, often of uncertain etiology, that have come to be known as the primary demyelinating diseases. Of these, multiple sclerosis is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Finally, there are animal models which mimic features of human demyelinating diseases [23]. Examples include experimental autoimmune neuritis (EAN), demyelination induced by Theiler's virus, and experimental autoimmune encephalomyelitis (EAE)—an autoimmune disease which is experimentally induced in a variety of species and which resembles MS in its clinical and neuropathological aspects [15, 21].

Multiple sclerosis (MS) is the most prevalent demyelinating condition. In Europe and North America, an average of 40–100 people out of every 100,000 have MS. The disease affects approximately 250,000 people in the United States alone. MS is a chronic, devastating neurological disease that affects mostly young adults. The pathogenesis of MS is a complex process that leads to destruction of myelin and oligodendroglia, as well as axonal damage, in the brain and spinal cord [1, 16]. Histopathologically, MS is characterized by inflammation, plaques of demyelination infiltrating cells in the CNS tissue, loss of oligodendroglia, and focal axonal injury [1]. The disease is thought to result from aberrant immune responses to myelin, and possibly non-myelin, self-antigens [17, 18]. Clinically, MS may follow a relapsing-remitting, or it may take a chronically progressive course with increasing physical disability [15]. Typically, the symptoms of MS include lack of co-ordination, paresthesias, speech and visual disturbances, and weakness [23].

Current treatments for the various demyelinating conditions are often expensive, symptomatic, and only partially effective, and may cause undesirable secondary effects. Corticosteroids (oral prednisone at 60–100 mg/day, tapered over 2–3 weeks, or intravenous methylprednisolone at 500–1000 mg/day, for 3–5 days) represent the main form of therapy for MS. While these may shorten the symptomatic period during attacks, they may not affect eventual long-term disability. Long-term corticosteroid treatment is rarely justified, and can cause numerous medical complications, including osteoporosis, ulcers, and diabetes [23].

Immunomodulatory therapy with recombinant human interferon-$\beta$ (Betaseron and Avonex) and with co-polymer (Copaxon) slightly reduces the frequency of relapses in MS, and may help delay eventual disability [23]. Both forms of interferon-$\beta$ and co-polymer are currently used as treatment modalities for MS, but all are exceedingly expensive. Immunosuppressive drugs (azathioprine, cladribine, cyclophosphamide, and methotrexate) are used for more severe progressive forms. However, they are not uniformly beneficial, and have significant toxic side-effects. Several drugs (e.g., baclofen at 30–60 mg/day in divided doses) may reduce spasticity by inhibiting the spinal cord reflexes. Cautious and judicious use is required, though, because the drug-induced reduction in spasticity in MS patients often exacerbates weakness, thereby further incapacitating the patient [23].

Similarly, current treatment for ALD, another devastating demyelinating disease, is relatively ineffective. Symptoms of ALD may include cortical blindness, corticospinal tract dysfunction, mental deterioration, and spasticity. Therapy to control the course of ALD may include bone marrow transplantation and dietary treatment [19], but inexorable neurological deterioration invariably occurs, ultimately leading to death [20, 23]. Some progress has been realized in the treatment of animals with EAE and EAN, by using glial cell transplants and growth factors, and by inhibiting adhesion molecules, autoantibodies, and cytokines [21]. However, none of these treatments has been shown to be beneficial in humans, and some require extensive neurosurgical intervention. Thus, it is clear from the foregoing that there exists a need for more effective, and less expensive and invasive, methods to treat the varied array of demyelinating conditions, without producing undesirable secondary effects.

Calcium-channel blockers are a class of pharmacological agents which inhibit the transmembrane flux of calcium ($Ca^{2+}$) ions into cells, particularly vascular smooth muscle cells and cardiac muscle cells. They have been indicated for the treatment of angina, arrhythmias, atrial fibrillation, hypertension, and paroxysmal supraventricular tachycardia [14]. Amlodipine, a potent $Ca^{2+}$-channel blocker, is a long-acting dihydropyridine calcium antagonist (calcium ion antagonist or slow-channel blocker). Amlodipine selectively inhibits $Ca^{2+}$-ion influx across cell membranes, with a greater effect on vascular smooth muscle cells than on cardiac muscle cells. In particular, amlodipine is a peripheral arterial vasodilator that acts directly on vascular smooth muscle to cause a reduction in peripheral vascular resistance and a reduction in blood pressure. Amlodipine has been demonstrated to be effective in treating chronic stable angina, vasospastic angina, and hypertension [14], and it may also have neuroprotective activity [12]. Other $Ca^{2+}$-channel blockers include bepridil, diltiazem, felodipine, flunarizine, isradipine, mibefradil, nicardipine, nifedipine, nimodipine, nisoldipine, nivaldipine, and verapamil [14].

SUMMARY OF THE INVENTION

The present invention is predicated on the discovery that a $Ca^{2+}$-channel blocker, amlodipine, can ameliorate the clinical impairment of a demyelinating condition, EAE, which is commonly used as a model of MS. On the basis of this finding, the present invention provides a method for treating a demyelinating condition in a subject in need of treatment, by administering to the subject an amount of a $Ca^{2+}$-channel blocker effective to treat the demyelinating condition.

The present invention is also directed to a method for treating a demyelinating condition in a subject in need of treatment, by administering to the subject a $Ca^{2+}$-channel blocker in combination with a glutamate inhibitor, in amounts effective to treat the demyelinating condition. Also provided is a pharmaceutical composition comprising a $Ca^{2+}$-channel blocker, a glutamate inhibitor, and a pharmaceutically-acceptable carrier.

Additionally, the present invention provides a method for treating a demyelinating condition in a subject in need of treatment, by administering to the subject a $Ca^{2+}$-channel blocker in combination with a hypertensive agent, in amounts effective to treat the demyelinating condition. The present invention also discloses a pharmaceutical composition comprising a $Ca^{2+}$-channel blocker, a hypertensive agent, and a pharmaceutically-acceptable carrier.

Additional objects of the present invention will be apparent in view of the description which follows.

DETAILED DESCRIPTION OF THE INVENTION

Figure 1:
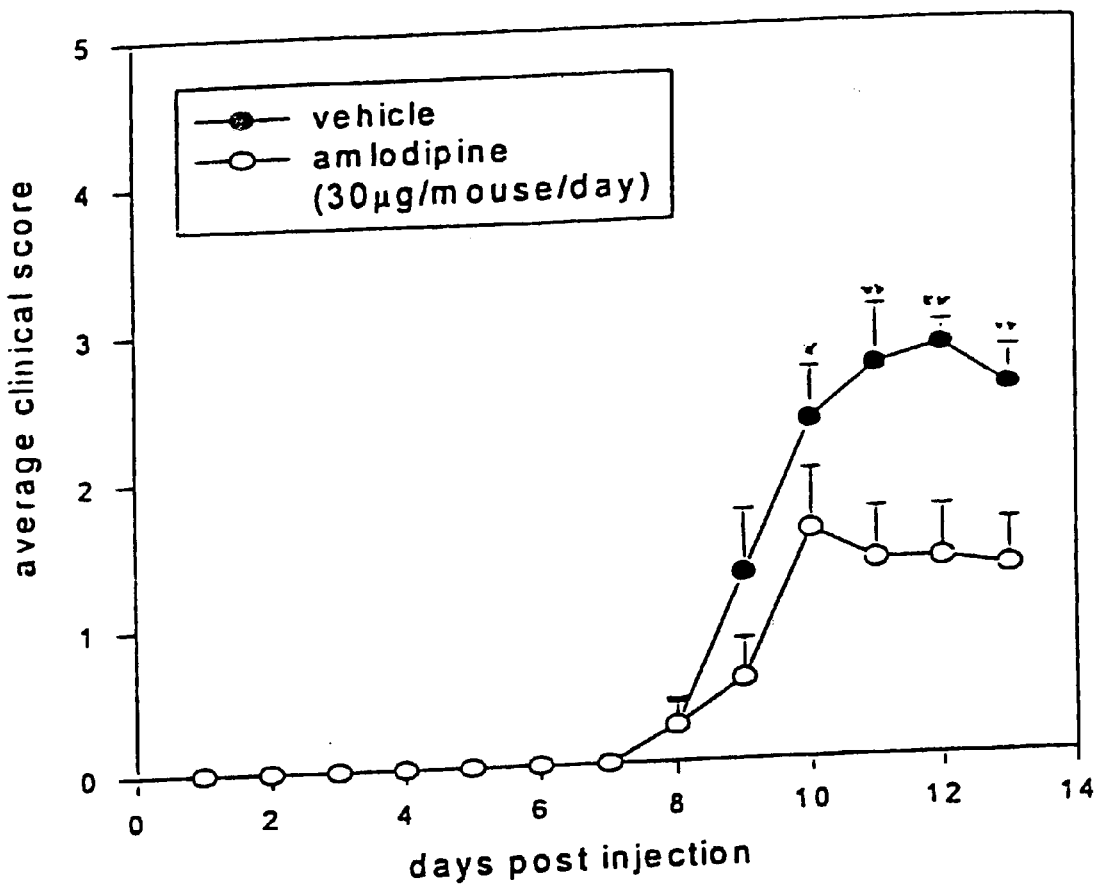
FIG. 1 illustrates the clinical course of adoptive-transfer EAE and the effect of treatment with amlodipine. SJL mice were injected with $3 \times 10^7$ MBP-activated cells. Starting from Day 5 post-immunization, mice were treated with amlodipine (30 µg as one daily subcutaneous injection) or vehicle (PBS), until Day 13 (Day 9 of treatment). Data represent mean ±s.e.m. differences, at respective time-points, between the vehicle-treated group and the amlodipine-treated group. *=p<0.05; **=p<0.01 (students' unpaired, two-tailed t-test); n=8 per group

The present invention is directed to a method for treating a demyelinating condition in a subject in need of treatment. The subject may be any mammal (e.g., dog, human, monkey), but is preferably a human. The method of the present invention comprises administering to the subject an amount of a calcium-channel blocker ($Ca^{2+}$-channel blocker) effective to treat the demyelinating condition in the subject. As used herein, the term "demyelinating condition" refers to a disease, disorder, or condition characterized by loss of myelin. Examples include, without limitation, acute disseminated encephalomyelitis (ADEM), acute transverse myelitis, acute viral encephalitis, adrenoleukodystrophy (ALD), adrenomyeloneuropathy, AIDS-vacuolar myelopathy, experimental autoimmune encephalomyelitis (EAE), experimental autoimmune neuritis (EAN), HTLV-associated myelopathy, Leber's hereditary optic atrophy, multiple sclerosis (MS), progressive multifocal leukoencephalopathy (PML), subacute sclerosing panencephalitis, and tropical spastic paraparesis. Preferably, the demyelinating condition is MS. Additionally, as used herein, the term "calcium-channel blocker" or "$Ca^{2+}$-channel blocker" refers to one of a class of pharmacological agents, also known as calcium antagonists, which inhibit the transmembrane flux of calcium ($Ca^{2+}$) ions.

As used herein, the term "agent" includes a protein, polypeptide, peptide, nucleic acid (including DNA or RNA), antibody, molecule, compound, antibiotic, drug, and any combinations thereof. $Ca^{2+}$-channel blockers are well-known in the art.

Examples of $Ca^{2+}$-channel blockers include, without limitation, amlodipine, bepridil, diltiazem, felodipine, flunarizine, isradipine, mibefradil, nicardipine, nifedipine, nimodipine, nisoldipine, nivaldipine, and verapamil. Preferably, the $Ca^{2+}$-channel blocker is amlodipine. As used herein, "amlodipine" refers to amlodipine and analogues thereof, including, for example, a functional variant of amlodipine which has amlodipine biological activity, as well as a fragment of amlodipine having amlodipine biological activity. As further used herein, the term "amlodipine biological activity" refers to amlodipine activity which ameliorates clinical impairment or symptoms of a demyelinating condition in a subject having a demyelinating condition.

Synthetic amlodipine is commercially available, and can be obtained from Pfizer Inc. (New York, N.Y.). Norvasc is the besylate salt of amlodipine. Norvasc tablets are formulated as white tablets, equivalent to 2.5, 5, and 10 mg of amlodipine, for oral administration. Amlodipine is an affordable compound; moreover, it provides a novel approach to treating demyelinating conditions based on pathophysiologic mechanisms [22]. As with other $Ca^{2+}$-channel blockers, though, amlodipine should be used with caution when treating subjects with heart failure [14].

The $Ca^{2+}$-channel blocker of the present invention is administered to a subject having a demyelinating condition in an amount which is effective to treat the demyelinating condition in the subject. As used herein, the phrase "effective to treat the demyelinating condition" means effective to ameliorate or minimize the clinical impairment or symptoms of the demyelinating condition. For example, where the demyelinating condition is MS, the amount of $Ca^{2+}$-channel blocker effective to treat the demyelinating condition is that which can ameliorate or minimize the symptoms of MS, including lack of co-ordination, paresthesias, speech and visual disturbances, and weakness. The amount of $Ca^{2+}$-channel blocker effective to treat a demyelinating condition in a subject will vary depending on the $Ca^{2+}$-channel blocker which is used. For example, the amount of amlodipine may range from about 5 mg/day to about 35 mg/day. Appropriate amounts of other $Ca^{2+}$-channel blockers effective to treat a demyelinating condition in a subject can be readily determined by the skilled artisan.

According to the method of the present invention, the $Ca^{2+}$-channel blocker may be administered to a human or animal subject by known procedures, including, but not limited to, oral administration, parenteral administration, transdermal administration, and administration through an osmotic mini-pump. Preferably, the $Ca^{2+}$-channel blocker is administered orally.

For oral administration, the formulation of the $Ca^{2+}$-channel blocker may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the $Ca^{2+}$-channel blocker may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be present in unit or multi-dose containers, such as sealed ampoules or vials. The formulation may be delivered by any mode of injection, including, without limitation, epifascial, intracapsular, intracutaneous, intramuscular, intraorbital, intraspinal, intrasternal, intravascular, intravenous, parenchymatous, or subcutaneous.

For transdermal administration, the $Ca^{2+}$-channel blocker may be combined with skin penetration enhancers, such as propylene glycol, polyethylene glycol, isopropanol, ethanol, oleic acid, N-methylpyrrolidone, and the like, which increase the permeability of the skin to the $Ca^{2+}$-channel blocker, and permit the $Ca^{2+}$-channel blocker to penetrate through the skin and into the bloodstream. The $Ca^{2+}$-channel blocker/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch.

The $Ca^{2+}$-channel blocker of the present invention also may be released or delivered from an osmotic mini-pump. The release rate from an elementary osmotic mini-pump may be modulated with a microporous, fast-response gel disposed in the release orifice. An osmotic mini-pump would be useful for controlling release of, or targeting delivery of, a $Ca^{2+}$-channel blocker, particularly a short-acting $Ca^{2+}$-channel blocker.

The present invention is also directed to a method for treating a demyelinating condition in a subject in need of treatment, comprising administering to the subject a $Ca^{2+}$-channel blocker in combination with a glutamate inhibitor, in amounts effective to treat the demyelinating condition. The demyelinating condition may be any of those described above. The $Ca^{2+}$-channel blocker may be any of those described above. Additionally, as used herein, the term "glutamate inhibitor" refers to any of a class of pharmacological agents which prevent the binding and/or action of glutamate (or glutamatergic agonists) at ionotropic glutamate receptors, resulting in reduced or completely blocked ion-conductance of such receptors. Examples of appropriate glutamate inhibitors include, without limitation, carbidopa, levodopa, and sodium-channel blockers.

In the method of the present invention, administration of a $Ca^{2+}$-channel blocker "in combination with" a glutamate inhibitor refers to co-administration of the two agents. Co-administration may occur concurrently, sequentially, or alternately. Concurrent co-administration refers to administration of both a $Ca^{2+}$-channel blocker and a glutamate inhibitor at essentially the same time. For concurrent co-administration, the courses of treatment with a $Ca^{2+}$-channel blocker and with a glutamate inhibitor may be run simultaneously. For example, a single, combined formulation, containing both an amount of a $Ca^{2+}$-channel blocker and an amount of a glutamate inhibitor in physical association with one another, may be administered to the subject. The single, combined formulation may consist of an oral formulation, containing amounts of both a $Ca^{2+}$-channel blocker and a glutamate inhibitor, which may be orally administered to the subject, or a liquid mixture, containing amounts of both a $Ca^{2+}$-channel blocker and a glutamate inhibitor, which may be injected into the subject.

It is also within the confines of the present invention that a $Ca^{2+}$-channel blocker and a glutamate inhibitor may be administered concurrently to a subject, in separate, individual formulations. Accordingly, the method of the present invention is not limited to concurrent co-administration of a $Ca^{2+}$-channel blocker and a glutamate inhibitor in physical association with one another.

In the method of the present invention, a $Ca^{2+}$-channel blocker and a glutamate inhibitor also may be co-administered to a subject in separate, individual formulations that are spaced out over a period of time, so as to obtain the maximum efficacy of the combination. Administration of each agent may range in duration, from a brief, rapid administration to a continuous perfusion. When spaced out over a period of time, co-administration of a $Ca^{2+}$-channel blocker and a glutamate inhibitor may be sequential or alternate. For sequential co-administration, one of the agents is separately administered, followed by the other. For example, a full course of treatment with a $Ca^{2+}$-channel blocker may be completed, and then may be followed by a full course of treatment with a glutamate inhibitor. Alternatively, for sequential co-administration, a full course of treatment with a glutamate inhibitor may be completed, then followed by a full course of treatment with a $Ca^{2+}$-channel blocker. For alternate co-administration, partial courses of treatment with a $Ca^{2+}$-channel blocker may be alternated with partial courses of treatment with a glutamate inhibitor, until a full treatment of each agent has been administered.

The agents of the present invention (i.e., a $Ca^{2+}$-channel blocker and a glutamate inhibitor, either in separate, individual formulations, or in a single, combined formulation) may be administered to a human or animal subject by any known procedures, including all of the above-described methods. Preferably, however, the $Ca^{2+}$-channel blocker and the glutamate inhibitor are co-administered orally.

In the method of the present invention, a $Ca^{2+}$-channel blocker and a glutamate inhibitor are co-administered in amounts effective to treat the demyelinating condition in the subject. As described above, this means that an amount of $Ca^{2+}$-channel blocker in combination with an amount of glutamate inhibitor is effective to ameliorate or minimize the clinical impairment or symptoms of the demyelinating condition. Appropriate amounts of a $Ca^{2+}$-channel blocker and a glutamate inhibitor effective to treat a demyelinating condition in a subject can be readily determined by the skilled artisan. A $Ca^{2+}$-channel blocker and a glutamate inhibitor may be co-administered to a subject in order to achieve a synergistic effect in the treatment of a demyelinating condition.

It is within the confines of the present invention that the formulations of a $Ca^{2+}$-channel blocker and a glutamate inhibitor (whether individual or combined) may be further associated with a pharmaceutically-acceptable carrier, thereby comprising a pharmaceutical composition. Accordingly, the present invention also discloses a pharmaceutical composition, comprising a $Ca^{2+}$-channel blocker, a glutamate inhibitor, and a pharmaceutically-acceptable carrier. Such a pharmaceutical composition would be useful for treating a demyelinating condition in a subject in need of treatment. Where the pharmaceutical composition is administered to a subject to treat a demyelinating condition, a $Ca^{2+}$-channel blocker and a glutamate inhibitor are provided in amounts which are effective to treat the demyelinating condition.

The pharmaceutically-acceptable carrier of the present invention must be "acceptable" in the sense of being compatible with the other ingredients of the composition, and not deleterious to the recipient thereof. Examples of acceptable pharmaceutical carriers include carboxymethylcellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may conveniently be presented in unit dosage.

The formulations of the present invention may be prepared by methods well-known in the pharmaceutical art. For example, the active compound may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the $Ca^{2+}$-channel blocker and the glutamate inhibitor of the present invention (either in separate, individual formulations, or in a single, combined formulation) to a subject to treat a demyelinating condition. The agents are provided in amounts that are effective to treat a demyelinating condition in the subject. These amounts may be readily determined by the skilled artisan.

The present invention also provides a method for treating a demyelinating condition in a subject in need of treatment, comprising administering to the subject a $Ca^{2+}$-channel blocker in combination with a hypertensive agent, in amounts effective to treat the demyelinating condition. The demyelinating condition may be any of those described above. The $Ca^{2+}$-channel blocker may be any of those described above. Additionally, as used herein, the term "hypertensive agent" refers to any of a class of pharmacological agents which increase blood pressure. As described above, an "agent" includes a protein, polypeptide, peptide, nucleic acid (including DNA or RNA), antibody, molecule, compound, antibiotic, drug, and any combinations thereof. Examples of appropriate hypertensive agents include, without limitation, phenylephrine (particularly phenylephrine that has been carefully titrated) and sodium chloride (NaCl).

In the method of the present invention, administration of a $Ca^{2+}$-channel blocker "in combination with" a hypertensive agent refers to co-administration of the two agents. As described above, co-administration may occur concurrently, sequentially, or alternately. A $Ca^{2+}$-channel blocker and a hypertensive agent may be co-administered by any of the above-described methods, and in any of the above-described formulations. For example, for concurrent co-administration, as described above, the courses of treatment with a $Ca^{2+}$-channel blocker and with a hypertensive agent may be run simultaneously, in a single, combined formulation containing both an amount of a $Ca^{2+}$-channel blocker and an amount of a hypertensive agent in physical association with one another. Alternatively, as described above, an amount of a $Ca^{2+}$-channel blocker and an amount of a hypertensive agent may be administered concurrently to a subject, in separate, individual formulations. Accordingly, the method of the present invention is not limited to concurrent co-administration of a $Ca^{2+}$-channel blocker and a hypertensive agent in physical association with one another.

In the method of the present invention, a $Ca^{2+}$-channel blocker and a hypertensive agent also may be co-administered to a subject in separate, individual formulations that are spaced out over a period of time, so as to obtain the maximum efficacy of the combination. Administration of each agent may range in duration, from a brief, rapid administration to a continuous perfusion. When spaced out over a period of time, co-administration of a $Ca^{2+}$-channel blocker and a hypertensive agent may be sequential or alternate, as described above.

The agents of the present invention (i.e., a $Ca^{2+}$-channel blocker and a hypertensive agent, either in separate, individual formulations, or in a single, combined formulation) may be administered to a human or animal subject by any known procedures, including all of the above-described methods. Preferably, however, the $Ca^{2+}$-channel blocker and the hypertensive agent are co-administered orally.

In the method of the present invention, a $Ca^{2+}$-channel blocker and a hypertensive agent are co-administered in amounts effective to treat the demyelinating condition in the subject. As described above, this means that an amount of $Ca^{2+}$-channel blocker in combination with an amount of hypertensive agent is effective to ameliorate or minimize the clinical impairment or symptoms of the demyelinating condition. Appropriate amounts of a $Ca^{2+}$-channel blocker and a hypertensive agent effective to treat a demyelinating condition in a subject can be readily determined by the skilled artisan. A $Ca^{2+}$-channel blocker and a hypertensive agent may be co-administered to a subject in order to achieve a synergistic effect in the treatment of a demyelinating condition.

It is within the confines of the present invention that the formulations of a $Ca^{2+}$-channel blocker and a hypertensive agent (whether individual or combined) may be further associated with a pharmaceutically-acceptable carrier, thereby comprising a pharmaceutical composition. Accordingly, the present invention also discloses a pharmaceutical composition comprising a $Ca^{2+}$-channel blocker, a hypertensive agent, and a pharmaceutically-acceptable carrier. Such a pharmaceutical composition would be useful for treating a demyelinating condition in a subject in need of treatment. Where the pharmaceutical composition is administered to a subject to treat a demyelinating condition, a $Ca^{2+}$-channel blocker and a hypertensive agent are provided in amounts which are effective to treat the demyelinating condition. The pharmaceutical composition of the present invention may be prepared in accordance with the methods, and in the formulations, described above.

The present invention is described in the following Experimental Details section, which is set forth to aid in the understanding of the invention, and should not be construed to limit in any way the scope of the invention as defined in the claims which follow thereafter.

EXPERIMENTAL DETAILS

1. Materials and Methods

A. Induction of Experimental Autoimmune Encephalomyelitis (EAE)

Adoptive-transfer EAE was induced in female SJL mice as described [13]. In brief, lymph node cells were obtained 10 days after myelin basic protein/Complete Freund's Adjuvant (MBP/CFA) immunization. Cells were cultured for 4 days with 50 µg/ml of MBP, then $3\times10^7$ cells/mouse were injected into syngeneic mice via tail veins. Onset of disease occurred after 7–9 days. Animals were graded according to a standard clinical index (0–5). Five days after immunization, animals began treatments with one daily injection of 200 µl of vehicle (PBS), or 30 µg of amlodipine in 200 µl of PBS.

B. Neuropathology

At selected time-points, mice from the control and treated groups were perfused with PBS or glutaraldehyde, and the CNS was prepared for frozen or 1-µm epoxy sections, respectively. Epoxy sections were stained with toluidine blue, and examined by light microscopy. Frozen sections were used for immunohistochemistry to evaluate damage to oligodendrocytes and neurons.

2. Results and Discussion

MS is characterized by destruction of myelin and oligodendrocytes in the CNS, as discussed above. One of the primary tools in MS research is experimental autoimmune encephalomyelitis (EAE), a demyelinating condition in animals which mimics many important aspects of the clinical and pathological features of MS [1, 15]. The mechanisms in MS which lead to myelin destruction and the demise of oligodendrocytes are currently unknown. Possible candidates are cell-cell contact involving inflammatory cells, and soluble factors such as TNF-α[2], metalloproteinases [3], reactive oxygen species (e.g., $O_2^-$ and $ONOO^-$) [4], and autoantibodies [5]. One soluble compound in particular, which is released in large quantities by activated leukocytes and microglia, has received little attention: glutamate. In activated immune cells, glutamate is produced and released by enzymatic breakdown of glutamine [6, 7]. However, in animals with EAE, glutamate degradation by astroglial glutamine synthase and glutamate dehydrogenase is diminished [9]. These findings suggest an increased extracellular glutamate concentration in and around the infiltrative lesion. This increase in glutamate is potentially disastrous in the mammalian CNS. The extracellular concentration of glutamate is tightly controlled in the CNS, and the glutamate gradient between extracellular and intracellular space is about 1:1000. If present in larger quantities, extracellular glutamate can cause excitotoxic cell death by overstimulation of the cellular ionotropic glutamate receptors, the NMDA and the AMPA/Kainate receptors [10, 11].

In a previous study, the present inventors were able to show that glutamate excitotoxicity mediated by AMPA/Kainate receptors accounted for a substantial portion of CNS damage in EAE [22]. Blockage of AMPA/Kainate receptors by NBQX, a prototypical AMPA/Kainate receptor antagonist, significantly ameliorated the course of the disease and reduced loss of oligodendrocytes and axonal damage. However, it was demonstrated, both in vitro and in vivo, that NBQX did not overtly affect the activity of the immune system [22]. Thus, the observed improvement resulted from direct protection against AMPA/Kainate-receptor-mediated excitotoxicity, rather than suppression of the immune response.

An important event downstream of AMPA/Kainate-receptor-mediated excitotoxicity is the opening of voltage-sensitive $Ca^{2+}$ channels, with subsequent excess $Ca^{2+}$ influx, which results in $Ca^{2+}$ overload and eventual excitotoxic damage [24]. Since the inventors had previously established a role for AMPA/Kainate receptor-mediated excitotoxicity in EAE, they investigated whether blockage of voltage-sensitive $Ca^{2+}$ channels might similarly reduce excitotoxic damage in this animal model of MS. The $Ca^{2+}$-channel antagonist amlodipine was selected for this study because of its long half-life in vivo (>30 h), and the beneficial effect on excitotoxic damage which it was shown to have in an in vitro model for excitotoxicity [12].

As the results of the present investigation show, 30 μg/day of amlodipine (in 200 μl of phosphate buffered saline [PBS]) significantly (p<0.01) ameliorated clinical impairment in the acute phase of the adoptive-transfer model of EAE. Mice (n=8) were treated from Day 5 post-immunization. The control group (n=8) received one daily subcutaneous injection of 200 μl of the vehicle PBS. The difference in clinical score was significant at Day 4 after onset of the disease, and continued to increase until the time of sampling (FIG. 1). The CNSs of two representative animals of each group were taken and examined as 1-μm epoxy sections stained with toluidine blue. The animals differed considerably in their clinical scoring, with an average score of 1.3 (amlodipine group) and 2.8 (control group). However, the examination of sections from the entire neuraxis (10 levels) showed a similar degree of inflammation and demyelination in both groups. This indicated that amlodipine does not modulate the inflammatory process itself—a result similar to that which was found with NBQX treatment.

In conclusion, the results show that amlodipine significantly (p<0.01) ameliorated the clinical impairment in acute EAE. However, examination of the neuraxis in both vehicle- and amlodipine-treated animals showed similar degrees of inflammation, indicating that amlodipine does not affect inflammation. The reduction in clinical impairment is, therefore, most likely due to amlodipine's protecting CNS cells against glutamate excitotoxicity via blockage of voltagesensitive $Ca^{2+}$ channels.

REFERENCES

1. Prineas and McDonald, Demyelinating Diseases. In *Greenfield's Neuropathology*, 6$^{th}$ ed. (Edward Arnold: New York, 1997) 813–81.
2. Akassoglou et al., Oligodendrocyte apoptosis and primary demyelination induced by local TNF/p55TNF receptor signaling in the central nervous system of transgenic mice: models for multiple sclerosis with primary oligodendrogliopathy. *Am. J. Path.*, 153(3):801–13, 1998.
3. Liedtke et al., Effective treatment of models of multiple sclerosis by matrix metalloproteinase inhibitors. *Ann. Neurol.*, 44:35–46, 1998.
4. Kolb and Kolb-Bachofen, Nitric oxide: a pathogenic factor in autoimmunity. *Immunol. Today*, 13(5):157–60, 1992.
5. Genain et al., Identification of autoantibodies associated with myelin damage in multiple sclerosis. *Nature Medicine*, 5(2):170–75, 1999.
6. Piani et al., Murine brain macrophages induce NMDA receptor mediated neurotoxicity in vitro by secreting glutamate. *Neurosci. Lett.*, 133:159–62, 1991.
7. Pithon et al., Glutamine utilization by rat neutrophils: presence of phosphate-dependent glutaminase. *Am. J. Phys.*, 273:C1124–29, 1997.
8. Raine, C. S., The lesion in multiple sclerosis and chronic relapsing experimental allergic encephalomyelitis: a structural comparison. In *Multiple Sclerosis Clinical and Pathogenetic Basis*, Raine, C. S., McFarland, H. F., and Tourtellotte, W. W., eds. (London: Chapman & Hall, 1997) 243–86.
9. Hardin-Pouzet et al., Glutamate metabolism is downregulated in astrocytes during experimental autoimmune encephalomyelitis. *Glia*, 20:79–85, 1997.
10. Rothman and Olney, Excitotoxicity and the NMDA receptor. *TINS* 10:299–302, 1987.
11. McDonald et al., Oligodendrocytes from forebrain are highly vulnerable to AMPA/Kainate receptor-mediated excitotoxicity. *Nature Medicine*, 4(3):291–97, 1998.
12. Mason et al., Inhibition of excessive neuronal apoptosis by the calcium antagonist amlodipine and antioxidants in cerebellar granule. *J. Neurochem.*, 72(4):1448–56, 1999.
13. Cannella et al., The neuregulin, glial growth factor 2, diminishes autoimmune demyelination and enhances remyelination in a chronic relapsing model for multiple sclerosis. *Proc. Natl. Acad. Sci. USA*, 95:10100–105, 1998.

14. *Physicians' Desk Reference*, 54th ed. (Montvale, N.J.: Medical Economics Company, Inc., 2000).
15. Gold et al., Animal models for autoimmune demyelinating disorders of the nervous system. *Mol. Med. Today*, 6:88–91, 2000.
16. Trapp et al., Axonal transection in the lesions of multiple sclerosis. *N. Engl. J. Med.*, 338:278–85, 1998.
17. Bar-Or et al., Molecular pathogenesis of multiple sclerosis. *J. Neuroimmunol.* 100:252–59, 1999.
18. Hartung, H.-P., Pathogenesis of inflammatory demyelination: implications for therapy. *Current Opinion in Neurology*, 8:191–99, 1995.
19. DiBiase et al., Adrenoleukodystrophy: genetics, phenotypes, pathogenesis, and treatment. *Ann. Ist. Super Sanita*, 35:185–92, 1999.
20. Krivit et al., Bone marrow transplantation for globoid cell leukodystrophy, adrenoleukodystrophy, metachromatic leukodystrophy, and Hurler syndrome. *Curr. Opin. Hematol.*, 6:377–82, 1999.
21. Njenga and Rodriguez, Animal models of demyelination. *Current Opinion in Neurology*, 9:159–64, 1996.
22. Pitt et al., Glutamate excitotoxicity in a model of multiple sclerosis. *Nature Medicine*, 6(1):67–70, 2000.
23. Beers and Berkow, eds., *The Merck Manual of Diagnosis and Therapy*, 17th ed. (Whitehouse Station, N.J.: Merck Research Laboratories, 1999) 1299, 1437, 1473–76, 1483.
24. Choi, D. W., Calcium-mediated neurotoxicity: relationship to specific channel types and role in ischemic damage. *Trends Neurosci.*, 11:465–69, 1988.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for treating multiple sclerosis in a subject in need of treatment, comprising administering to the subject an amount of amlodipine effective to treat the multiple sclerosis in the subject.

2. The method of claim 1, wherein the amlodipine is administered orally.

3. The method of claim 1, wherein the amlodipine is administered parenterally.

4. The method of claim 1, wherein the amlodipine is administered by an osmotic mini-pump.

5. A method for treating multiple sclerosis in a subject in need of treatment, comprising administering to the subject amlodipine in combination with a glutamate inhibitor, in amounts effective to treat the multiple sclerosis.

6. A pharmaceutical composition comprising amlodipine, a glutamate inhibitor, and a pharmaceutically-acceptable carrier.

* * * * *